(12) United States Patent
Yoo et al.

(10) Patent No.: US 10,167,425 B2
(45) Date of Patent: Jan. 1, 2019

(54) ETCHING SOLUTION CAPABLE OF SUPPRESSING PARTICLE APPEARANCE

(71) Applicant: OCI COMPANY LTD., Seoul (KR)

(72) Inventors: Hoseong Yoo, Seongnam-si (KR); Seunghyun Han, Seongham-si (KR); Wook Chang, Seongnam-si (KR); Yongil Kim, Seongnam-si (KR)

(73) Assignee: OCI COMPANY LTD., Seoul (KR)

( * ) Notice: Subject to any disclaimer, the term of this patent is extended or adjusted under 35 U.S.C. 154(b) by 0 days.

(21) Appl. No.: 15/584,208

(22) Filed: May 2, 2017

(65) Prior Publication Data

US 2017/0321121 A1    Nov. 9, 2017

(30) Foreign Application Priority Data

May 4, 2016    (KR) .................. 10-2016-0055284
May 19, 2016    (KR) .................. 10-2016-0061281

(51) Int. Cl.
| | | |
|---|---|---|
| *C09K 13/08* | (2006.01) | |
| *C07C 69/34* | (2006.01) | |
| *C07C 69/02* | (2006.01) | |
| *H01L 21/02* | (2006.01) | |
| *C08K 5/54* | (2006.01) | |
| *C01B 7/19* | (2006.01) | |

(52) U.S. Cl.
CPC ............... *C09K 13/08* (2013.01); *C01B 7/19* (2013.01); *C07C 69/02* (2013.01); *C07C 69/34* (2013.01); *C08K 5/54* (2013.01); *H01L 21/02019* (2013.01)

(58) Field of Classification Search
CPC .......... C09K 13/08; C09K 5/54; C07C 69/02; C07C 69/34; H01L 21/02019; C01B 7/19
See application file for complete search history.

(56) References Cited

U.S. PATENT DOCUMENTS

| 6,646,348 B1 * | 11/2003 | Grumbine | C09G 1/02 257/752 |
|---|---|---|---|
| 9,868,902 B2 * | 1/2018 | Lee | C09K 13/06 |
| 2009/0192065 A1 * | 7/2009 | Korzenski | C11D 7/08 510/176 |
| 2010/0007031 A1 * | 1/2010 | Kobayashi | C11D 3/042 257/774 |
| 2015/0348799 A1 * | 12/2015 | Hong | C09K 13/04 438/268 |
| 2016/0017224 A1 * | 1/2016 | Lee | C09K 13/06 438/706 |

FOREIGN PATENT DOCUMENTS

| CN | 105273718 A | 1/2016 |
|---|---|---|
| KR | 101032093 B1 | 5/2011 |
| TW | 200710205 A | 3/2007 |
| TW | 200849389 A | 12/2008 |

OTHER PUBLICATIONS

Twianese Office Action dated Dec. 25, 2017, in connection with the counterpart Twianese Patent Application No. 10621297500.
Korean Office Action dated Feb. 13, 2018, in connection with the counterpart Korean Patent Application No. 1020160061281.
Chinese Office Action dated Aug. 8, 2018, issued in corresponding Chinese Patent Application No. 201710300690.6.

* cited by examiner

*Primary Examiner* — Anita K Alanko
(74) *Attorney, Agent, or Firm* — Hauptman Ham, LLP

(57) ABSTRACT

The present disclosure relates to an etching solution capable of suppressing particle appearance including a first silane compound in which three or more hydrophilic functional groups are independently bonded to a silicon atom and a second silane compound in which one or two hydrophilic functional groups are independently bonded to a silicon atom.

10 Claims, No Drawings

ETCHING SOLUTION CAPABLE OF SUPPRESSING PARTICLE APPEARANCE

CROSS-REFERENCE TO RELATED APPLICATIONS

This application claims the priority of Korean Patent Application No. 10-2016-0055284 filed on May 4, 2016 and Korean Patent Application No. 10-2016-0061281 filed on May 19, 2016, in the Korean Intellectual Property Office, the disclosure of which is hereby incorporated by reference in its entirety.

BACKGROUND

1. Technical Field

The present disclosure relates to an etching solution capable of suppressing appearance of silicon based particles after silicon nitride etching is completed.

2. Description of the Related Art

Using phosphoric acid as an etchant for silicon nitride layer is a well-known method.

High selectivity is not possible when pure phosphoric acid is used because phosphoric acid etches both silicon nitride and silicon oxide. Therefore, problems such as defects, pattern abnormalities, and particle appearance arise during etching process.

Meanwhile, there is an attempt to use a fluorine-containing compound as an additive to further increase the etching rate of the silicon nitride layer. However, fluorine also increases the etching rate for the silicon nitride layer.

In recent years, silicon additives are added to the phosphoric acid to decrease the silicon oxide layer to achieve high selectivity. Since a silane compound mainly used as the silicon additive has a low solubility to an etching solution including phosphoric acid, a silane compound in which a hydrophilic functional group (e.g., A group capable of hydrogen bonding) is bonded to a silicon atom is used to increase the solubility of the silane compound in the phosphoric acid solution When functional group is present in the silane, solubility of the compound will increase in phosphoric acid; thus, an appropriate solubility of the silane compound to the etching solution may be secured. However, when concentration of the silane compound in the etching solution is increased to suppress silicon oxide E/R (Etching Rate), selectivity also drops due to suppressing silicon nitride E/R as well.

Furthermore, if too much silicon additives are used, silicon additives will bond together to create uncontrollable particle size results in wafer and particle bond that creates wafer defection.

SUMMARY

It is an object of the present disclosure to provide an etching solution for a silicon nitride layer capable of increasing a selectivity of a silicon nitride layer to a silicon oxide layer by using a silane compound-based silicon additive.

It is another object of the present disclosure to provide an etching solution for a silicon nitride layer capable of compensating for an etching rate reduced due to the use of the silicon additive, by using a fluorine-containing compound.

Objects of the present disclosure are not limited to the above-described objects and other objects and advantages can be appreciated by those skilled in the art from the following descriptions. Further, it will be easily appreciated that the objects and advantages of the present disclosure can be practiced by means recited in the appended claims and a combination thereof.

In accordance with one aspect of the present disclosure, an etching solution for a silicon nitride layer includes: an aqueous solution including at least one acid of an inorganic acid and an organic acid; a first silane compound including 1 to 6 silicon atoms where at least one silicon atom is bonded to three or more hydrophilic functional groups; a second silane compound including 1 to 6 silicon atoms where the number of hydrophilic functional groups bonded to one silicon atom is a maximum of 2; and a fluorine-containing compound.

The hydrophilic functional group may be a hydroxyl group or a functional group substitutable with a hydroxy group under a pH condition of The etching solution capable of suppressing particle appearance.

In accordance with another aspect of the present disclosure, there is provided a post-etching cleaning solution capable of reducing or suppressing occurrence of silicon-based particles at the time of cleaning after a silicon substrate is etched with an etching solution including a silicon additive.

DETAILED DESCRIPTION

The above objects, features and advantages will become apparent from the detailed description with reference to the accompanying drawings. Embodiments are described in sufficient detail to enable those skilled in the art in the art to easily practice the technical idea of the present disclosure. Detailed descriptions of well known functions or configurations may be omitted in order not to unnecessarily obscure the gist of the present disclosure. Hereinafter, embodiments of the present disclosure will be described in detail with reference to the accompanying drawings. Throughout the drawings, like reference numerals refer to like elements.

According to an exemplary embodiment of the present disclosure, an etching solution for a silicon nitride layer may include an aqueous solution including at least one acid of an inorganic acid and an organic acid (hereinafter, referred to as an acid aqueous solution), a first silane compound including 1 to 6 silicon atoms where at least one silicon atom is bonded to three or more hydrophilic functional groups, a second silane compound including 1 to 6 silicon atoms where the number of hydrophilic functional groups bonded to one silicon atom is a maximum of 2, and a fluorine-containing compound.

Here, the inorganic acid may be at least one selected from sulfuric acid, nitric acid, phosphoric acid, silicic acid, hydrofluoric acid, boric acid, hydrochloric acid, and perchloric acid. In addition, phosphoric anhydride, pyrophosphoric acid or polyphosphoric acid may be used in addition to the above-described inorganic acids.

Here, the organic acid may be at least one selected from acetic acid, citric acid, formic acid, gluconic acid, lactic acid, oxalic acid, tartaric acid and hydrogen carbonic acid. Further, organic acids such as propionic acid, butyric acid, palmitic acid, stearic acid, oleic acid, malonic acid, succinic acid, maleic acid, glycolic acid, glutaric acid, adipic acid, sulfosuccinic acid, valeric acid, caproic acid, capric acid, lauric acid, myristic acid, lactic acid, malic acid, citric acid, tartaric acid, benzoic acid, salicylic acid, para-toluenesulfonic acid, naphthoic acid, nicotinic acid, toluic acid, anisic acid, cuminic acid, and phthalic acid may be used in addition to the above-described organic acids. If necessary, an acid aqueous solution including a mixed acid of the inorganic acid and the organic acid may be used.

Here, the inorganic acid and the organic acid may be present in a form of a salt in an aqueous solution, and the salt preferably has a form of an ammonium salt.

The acid aqueous solution is a component that maintains pH of the etching solution to suppress various types of silane compounds present in the etching solution from changing into silicon-based particles.

In an exemplary embodiment, the acid aqueous solution preferably has a content of 60 to 90 parts by weight based on 100 parts by weight of The etching solution capable of suppressing particle appearance.

When the content of the acid aqueous solution is less than 60 parts by weight based on 100 parts by weight of The etching solution capable of suppressing particle appearance, the etching rate of the silicon nitride layer may be reduced, and thus, the silicon nitride layer may not be sufficiently etched or a process efficiency in etching the silicon nitride layer may be reduced.

On the other hand, when the content of the acid aqueous solution is more than 90 parts by weight based on 100 parts by weight of The etching solution capable of suppressing particle appearance, not only the etching rate of the silicon nitride layer may be excessively increased but also the selectivity of the silicon nitride layer to the silicon oxide layer may be reduced since the silicon oxide layer is rapidly etched. Further, as the silicon oxide layer is etched, defects of the silicon substrate may be caused.

The etching solution capable of suppressing particle appearance according to an exemplary embodiment of the present disclosure includes a first silane compound represented by Chemical Formula 1 below or Chemical Formula 2 below to increase the selectivity of the silicon nitride layer to the silicon oxide layer.

As represented by Chemical Formula 1 below, the first silane compound of the present disclosure may be defined as a compound in which functional groups of $R_1$ to $R_4$ are bonded to one silicon atom. Here, at least three of $R_1$ to $R_4$ are hydrophilic functional groups.

[Chemical Formula 1]

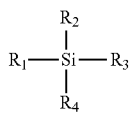

In Chemical Formula 1, $R_1$ to $R_4$ are each independently a hydrophilic functional group or is a functional group selected from hydrogen, $C_1$-$C_{10}$ alkyl, $C_6$-$C_{12}$ cycloalkyl, $C_2$-$C_{10}$ heteroalkyl including at least one heteroatom, $C_2$-$C_{10}$ alkenyl, $C_2$-$C_{10}$ alkynyl, $C_1$-$C_{10}$ haloalkyl, $C_1$-$C_{10}$ aminoalkyl, aryl, heteroaryl, aralkyl, silyloxy, and siloxane.

Further, as represented by Chemical Formula 2 below, the first silane compound of the present disclosure may be defined as a silane compound in which at least two silicon atoms are continuously bonded:

[Chemical Formula 2]

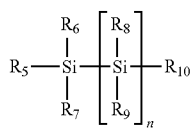

in Chemical Formula 2, $R_5$ to $R_{10}$ are each independently a hydrophilic functional group or is a functional group selected from hydrogen, $C_1$-$C_{10}$ alkyl, $C_6$-$C_{12}$ cycloalkyl, $C_2$-$C_{10}$ heteroalkyl including at least one heteroatom, $C_2$-$C_{10}$ alkenyl, $C_2$-$C_{10}$ alkynyl, $C_1$-$C_{10}$ haloalkyl, $C_1$-$C_{10}$ aminoalkyl, aryl, heteroaryl, aralkyl, silyloxy, and siloxane, and n is an integer of 1 to 5.

That is, the first silane compound includes 1 to 6 silicon atoms, and specifically includes at least one silicon atom to which three or more hydrophilic functional groups are bonded, and thus, it is possible to secure sufficient solubility in an etching solution for a silicon nitride layer including an acid aqueous solution, and it is possible to form relatively strong hydrophilic interaction with a silicon substrate, particularly a silicon oxide layer.

The first silane compound attached to a surface of the silicon oxide layer through the strong hydrophilic interaction may prevent the silicon substrate from being etched by the inorganic acid of the silicon oxide layer or the fluorine-containing compound.

The hydrophilic functional group bonded to the silicon atom is a hydroxy group or a functional group substitutable with a hydroxy group under a pH condition of the acid aqueous solution.

Here, non-limiting examples of the functional group substitutable with a hydroxy group under a pH condition of the acid aqueous solution include an amino group, a halogen group, a sulfonic group, a phosphonic group, a phosphoric group, a thiol group, an alkoxy group, an amide group, an ester group, an acid anhydride group, an acyl halide group, a cyano group, a carboxyl group, and an azole group. Thus, the functional group substitutable with a hydroxy group under a pH condition of the acid aqueous solution is not necessarily limited to the above-described functional groups, and should be understood to include any functional group substitutable with a hydroxy group under a pH condition of the acid aqueous solution.

The pH condition of the acid aqueous solution in the present disclosure means 4 or less. When the pH condition of the acid aqueous solution is more than 4, stability of the first silane compound present in The etching solution capable of suppressing particle appearance may be decreased due to the relatively high pH, and thus, the silane compound may act as a source of the silicon-based particle.

The halogen in the present disclosure means fluoro (—F), chloro (—Cl), bromo (—Br) or iodo (—I), and the haloalkyl refers to alkyl substituted with the above-described halogen. For example, halomethyl means methyl (—$CH_2X$, —$CHX_2$ or —$CX_3$) in which at least one of hydrogen of methyl is substituted with halogen.

In addition, the alkoxy in the present disclosure means both an —O— (alkyl) group and an —O— (unsubstituted cycloalkyl) group, and is a linear or branched hydrocarbon having one or more ether groups and 1 to 10 carbon atoms.

Specifically, the alkoxy includes methoxy, ethoxy, propoxy, isopropoxy, n-butoxy, tert-butoxy, sec-butoxy, n-pentoxy, n-hexoxy, 1,2-dimethylbutoxy, cyclopropyloxy, cyclobutyloxy, cyclopentyloxy, cyclohexyloxy, etc., but is not limited thereto.

When $R_a$ (wherein a is an integer selected from 1 to 4) is alkenyl or alkynyl, a $sp^2$-hybrid carbon of the alkenyl or a $sp^3$-hybrid carbon of the alkynyl may be directly bonded or may be indirectly bonded by a $sp^3$-hybrid carbon of an alkyl bonded to the $sp^2$-hybrid carbon of the alkenyl or the sp-hybrid carbon of the alkynyl.

A $C_a$-$C_b$ functional group herein means a functional group in which the number of carbon atoms is a to b. For example, the $C_a$-$C_b$ alkyl means a saturated aliphatic group, including linear alkyl and branched alkyl in which the number of carbon atoms is a to b. The linear alkyl or branched alkyl has carbon atoms of 10 or less (for example, $C_1$-$C_{10}$ straight chain, $C_3$-$C_{10}$ branched chain), preferably 4 or less, and more preferably 3 or less, in a main chain thereof.

Specifically, the alkyl may be methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, n-heptyl, and n-octyl.

The aryl used herein means an unsaturated aromatic ring including a single ring or multiple rings (preferably one to four rings) conjugated or covalently bonded to each other, unless otherwise defined. Non-limiting examples of the aryl include phenyl, biphenyl, o-terphenyl, m-terphenyl, p-terphenyl, 1-naphthyl, 2-naphthyl, 1-anthryl, 2-anthryl, 9-anthryl, 1-phenanthrenyl, 2-phenanthrenyl, 3-phenanthrenyl, 4-phenanthrenyl, 9-phenanthrenyl, 1-pyrenyl, 2-pyrenyl, and 4-pyrenyl, etc.

The heteroaryl used herein means a functional group in which one or more carbon atoms in the aryl as defined above are substituted with a non-carbon atom such as nitrogen, oxygen or sulfur.

Non-limiting examples of the heteroaryl include furyl, tetrahydrofuryl, pyrrolyl, pyrrolidinyl, thienyl, tetrahydrothienyl, oxazolyl, isoxazolyl, triazolyl, thiazolyl, isothiazolyl, pyrazolyl, pyrazolidinyl, oxadiazolyl, thiadiazolyl, imidazolyl, imidazolinyl, pyridyl, pyridaziyl, triazinyl, piperidinyl, morpholinyl, thiomorpholinyl, pyrazinyl, piperainyl, pyrimidinyl, naphthyridinyl, benzofuranyl, benzothienyl, indolyl, indolynyl, indolizinyl, indazolyl, quinolizinyl, quinolinyl, isoquinolinyl, cinnolinyl, phthalazinyl, quinazolinyl, quinoxalinyl, pteridinyl, quinuclidinyl, carbazoyl, acridinyl, phenazinyl, phenothizinyl, phenoxazinyl, purinyl, benzimidazolyl, benzothiazolyl, etc., and analogues to which these are conjugated.

The aralkyl used herein is a functional group of a form in which aryl is substituted with carbon of the alkyl, and has a generic formula of —$(CH_2)_n$Ar. Examples of the aralkyl include benzyl (—$CH_2C_6H_5$) or phenethyl (—$CH_2CH_2C_6H_5$), etc.

A hydrocarbon ring (hereinafter, referred to as cycloalkyl) or a hydrocarbon ring including a heteroatom (hereinafter, referred to as heterocycloalkyl) used herein may be understood as a cyclic structure of alkyl or a cyclic structure of heteroalkyl, respectively, unless otherwise defined.

Non-limiting examples of the cycloalkyl include cyclopentyl, cyclohexyl, 1-cyclohexenyl, 3-cyclohexenyl, and cycloheptyl, etc.

Non-limiting examples of the heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, and 2-piperazinyl, etc.

Further, the cycloalkyl or the heterocycloalkyl may be conjugated with another cycloalkyl, another heterocycloalkyl, aryl or heteroaryl, or may be covalently bonded therewith.

The silyloxy used herein is a functional group of a form in which silyl is substituted with oxygen, and has a generic formula of —O—Si(R)$_3$.

The first silane compound is preferably present at 100 to 10,000 ppm in etching solution for a silicon nitride layer.

When the first silane compound in The etching solution capable of suppressing particle appearance is present at less than 100 ppm, an effect of increasing the selectivity of the silicon nitride layer to the silicon oxide layer may not be sufficient. On the other hand, when the first silane compound in The etching solution capable of suppressing particle appearance is more than 10,000 ppm, the etching rate of the silicon nitride layer may be rather decreased according to the increased silicon concentration in The etching solution capable of suppressing particle appearance, and the first silane compound itself may act as the source of the silicon-based particle.

The etching solution capable of suppressing particle appearance according to an exemplary embodiment of the present disclosure may include the first silane compound as a silicon additive to compensate for the decreased etching rate of the silicon nitride layer, and at the same time, may further include a fluorine-containing compound to improve an efficiency of the overall etching process.

The fluorine-containing compound used herein refers to any type of compound capable of dissociating fluorine ions.

In an exemplary embodiment, the fluorine-containing compound is at least one selected from hydrogen fluoride, ammonium fluoride, ammonium bifluoride, and ammonium hydrogen fluoride.

Further, in another exemplary embodiment, the fluorine-containing compound may be a compound in which an organic cation and a fluorine-based anion are ionically bonded.

For example, the fluorine-containing compound may be a compound in which alkylammonium and the fluorine-based anion are ionically bonded. Here, the alkylammonium is an ammonium having at least one alkyl group, and may have the maximum of four alkyl groups. The alkyl group is defined as above.

As another examples thereof, the fluorine-containing compound may be an ionic liquid in which an organic cation and a fluorine-based anion are ionically bonded, the organic cation being selected from alkylpyrrolium, alkylimidazolium, alkylpyrazolium, alkyloxazolium, alkylthiazolium, alkylpyridinium, alkylpyrimidinium, alkylpyridazinium, alkylpyrazinium, alkylpyrrolidinium, alkylphosphonium, alkylmorpholinium, and alkylpiperidinium, and the fluorine-based anion being selected from fluorophosphate, fluoroalkyl-fluorophosphate, fluoroborate, and fluoroalkyl-fluoroborate.

The fluorine-containing compound which is provided in the form of the ionic liquid has a high boiling point and a high decomposition temperature as compared to hydrogen fluoride or ammonium fluoride which is generally used as the fluorine-containing compound in The etching solution capable of suppressing particle appearance. Accordingly, there is an advantage in that there is less concern to change the composition of the etching solution due to decomposition in the etching process performed at a high temperature.

However, when an excessive content of fluorine or fluorine ions remain in the etching solution due to the inclusion of the excessive fluorine-containing compound in The etching solution capable of suppressing particle appearance, the etching rate of the silicon nitride layer as well as the etching rate of the silicon oxide layer may be increased.

According to the present disclosure regarding this, a second silane compound represented by Chemical Formula 3 or 4 is additionally included in The etching solution capable of suppressing particle appearance, and thus, it is possible to suppress the problem of the increase in etching rate of the silicon oxide layer caused by the fluorine-containing compound.

As represented by Chemical Formula 3 below, the second silane compound of the present disclosure may be defined as a compound in which functional groups of $R_{11}$ to $R_{14}$ are bonded to one silicon atom. Here, the number of hydrophilic functional groups is one or two among $R_{11}$ to $R_{14}$.

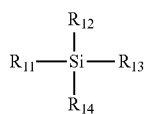

[Chemical Formula 3]

In Chemical Formula 3, $R_{11}$ to $R_{14}$ are each independently a hydrophilic functional group or a functional group selected from hydrogen, $C_1$-$C_{10}$ alkyl, $C_6$-$C_{12}$ cycloalkyl, $C_2$-$C_{10}$ heteroalkyl including at least one heteroatom, $C_2$-$C_{10}$ alkenyl, $C_2$-$C_{10}$ alkynyl, $C_1$-$C_{10}$ haloalkyl, $C_1$-$C_{10}$ aminoalkyl, aryl, heteroaryl, aralkyl, silyloxy, and siloxane.

Further, as represented by Chemical Formula 4 below, the second silane compound of the present disclosure may be defined as a silane compound in which at least two silicon atoms are continuously bonded:

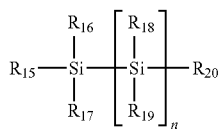

[Chemical Formula 4]

in Chemical Formula 2, $R_{15}$ to $R_{20}$ are each independently a hydrophilic functional group or a functional group selected from hydrogen, $C_1$-$C_{10}$ alkyl, $C_6$-$C_{12}$ cycloalkyl, $C_2$-$C_{10}$ heteroalkyl including at least one heteroatom, $C_2$-$C_{10}$ alkenyl, $C_2$-$C_{10}$ alkynyl, $C_1$-$C_{10}$ haloalkyl, $C_1$-$C_{10}$ aminoalkyl, aryl, heteroaryl, aralkyl, silyloxy, and siloxane, and n is an integer of 1 to 5.

That is, the second silane compound includes 1 to 6 silicon atoms, and includes the hydrophilic functional group bonded to the silicon atom, thereby securing an appropriate level of solubility in The etching solution capable of suppressing particle appearance including the acid aqueous solution.

Accordingly, the second silane compound which is present in a properly dissolved state in The etching solution capable of suppressing particle appearance may appropriately react with the fluorine-containing compound present in an excessive content relative to the first silane compound, thereby preventing an increase in the etching rate of the silicon oxide layer.

Further, the second silane compound has a smaller number of hydrophilic functional groups than the first silane compound, and thus, a possibility of acting as a nucleus of the silicon-based particles may be minimized.

In particular, the second silane compound has a maximum of two hydrophilic functional groups to ensure solubility in The etching solution capable of suppressing particle appearance, thereby having a maximum of two silicon-hydroxy groups (—Si—OH) under pH conditions of the acid aqueous solution.

Here, the description in which the second silane compound has a maximum of two hydrophilic functional groups means that the number of hydrophilic functional groups bonded to one silicon atom is a maximum of two. Further, it is preferred that the second silane compound has at least one hydrophilic functional group in order to secure solubility in etching solution for a silicon nitride layer.

Accordingly, when there is one silicon atom forming the second silane compound, it is preferred that the number of hydrophilic functional groups among the four functional groups bonded to the silicon atom is one or two. Further, when the number of silicon atoms forming the second silane compound is two or more, it is preferred to include at least one silicon atom bonded to the maximum of two hydrophilic functional groups.

Here, when the hydrophilic functional group in the second silane compound is substituted with a silicon-hydroxy group (—Si—OH) under the pH condition of the acid aqueous solution, the second silane compound is polymerized with the first silane compound or the second silane compound via the silicon-hydroxy group (—Si—OH) to grow into a silicone dimer, a silicone oligomer or a silicone oil having a regular one-dimensional or two-dimensional arrangement, and thus, the occurrence of the silicon-based particles due to the random growth may be prevented in advance.

The second silane compound is preferably present at 100 to 30,000 ppm in etching solution for a silicon nitride layer. When the second silane compound is present at a concentration of less than 100 ppm in The etching solution capable of suppressing particle appearance, it may be difficult to suppress the etching of the silicon oxide layer by the fluorine-containing compound present in an excessive content and it may be difficult to suppress the occurrence of the silicon-based particles caused by the first silane compound.

As described above, The etching solution capable of suppressing particle appearance according to the present disclosure may maintain a high selectivity of the silicon nitride layer to the silicon oxide layer and simultaneously may control the occurrence of silicon-based particles during etching or cleaning after etching.

Accordingly, when the silicon nitride layer is etched at 165° C. for 1 minute with The etching solution capable of suppressing particle appearance according to the present disclosure, an average diameter of the occurred silicon-based particles may be 0.1 μm or less.

According to another aspect of the present disclosure, there is provided a post-etching cleaning solution capable of reducing or suppressing occurrence of silicon-based particles at the time of cleaning after a silicon substrate (wafer) is etched with an etching solution including a silicon additive.

More specifically, the post-etching cleaning solution according to an exemplary embodiment of the present disclosure may include an acid aqueous solution and a second silane compound represented by Chemical Formula 3 or 4. Here, the definitions of the acid aqueous solution and the second silane compound are the same as defined in The etching solution capable of suppressing particle appearance, unless otherwise defined.

Here, the acid aqueous solution is a component that removes the silicon-based particles in a nanometer unit that occur during the etching, and simultaneously suppress the silane compound present in the cleaning solution from changing into the silicon-based particles by maintaining the pH of the cleaning solution.

In addition, at the time of cleaning after the silicon substrate is etched with the etching solution including the silicon additive, an acid in the acid aqueous solution may dissolve or disperse various contaminants (including nanometer-sized silicon-based particles) present in the silicon substrate. Accordingly, at the time of secondary cleaning using deionized water, etc., after primary cleaning of the silicon substrate using the cleaning solution, various contaminants may be easily removed from the silicon substrate.

In an exemplary embodiment, the acid aqueous solution preferably has a content of 60 to 95 parts by weight based on 100 parts by weight of the cleaning solution.

When the content of the acid aqueous solution is less than 60 parts by weight based on 100 parts by weight of the cleaning solution, silicon-based particles occur from the silicon-based additive used in the etching solution remaining on the silicon substrate after etching due to the increase in pH of the cleaning solution, and thus, efficiency of a cleaning process may be reduced.

On the other hand, when the content of the acid aqueous solution is more than 95 parts by weight based on 100 parts by weight of the cleaning solution, viscosity of the acid aqueous solution may be excessively high, and thus, fluidity of the cleaning solution may be reduced. When the fluidity of the acid aqueous solution is reduced, efficiency of the cleaning process may be reduced or a surface of the silicon substrate may be damaged. For example, a surface damage of the silicon substrate may include pattern defects, etc., due to the etching of the silicon oxide layer.

In addition, a water content in the acid aqueous solution is preferably 40% by weight or less, and more preferably 5 to 15% by weight.

When the water content in the acid aqueous solution is more than 40% by weight, the silicon-based particles may occur from the silicon additive used in the etching solution remaining on the silicon substrate due to the increase in the pH of the cleaning solution. On the other hand, when the water content in the acid aqueous solution is less than 5% by weight, not only the fluidity of the cleaning solution may be reduced but also the silicon substrate may be over-etched as a result of the etching of the silicon substrate by the cleaning solution.

In addition, the pH of the acid aqueous solution including the inorganic acid and/or the organic acid is preferably 4 or less.

When the pH of the acid aqueous solution is more than 4, the silicon-based particles may occur from the silicon additive used in the etching solution remaining on the silicon substrate due to the excessive content of water included in the cleaning solution and high pH.

The second silane compound represented by Chemical Formula 3 or 4 has a form in which at least one or at most two hydrophilic functional group are bonded to one silicon atom, and it is possible to sufficiently secure solubility in the cleaning solution including the acid aqueous solution.

In addition, the second silane compound represented by Chemical Formula 3 or 4 has a maximum of two hydrophilic functional groups, and thus, there is little possibility that the silane compound itself acts as a source of silicon-based particles at the time of cleaning.

The second silane compound having a maximum of two silicon-hydroxy groups (—Si—OH) under the pH condition of the acid aqueous solution is polymerized with the silicon-hydroxy group (—Si—OH) present in the silicon-based particles having a size of several nanometers present on the silicon substrate after etching to produce a silicon-siloxane compound.

Here, unlike the second silane compound represented by Chemical Formula 3 or 4, when the number of hydrophilic functional groups bonded to the silicon atom forming the silane compound is 3 or more (for example, the first silane compound), and when the silane compound having the silicon-hydroxy group is polymerized with silicon-based particles having a size of several nanometers, random growth may be achieved because the number of polymerizable functional groups is relatively large. Accordingly, there is a risk that micrometer-sized silicon-based particles may occur.

Thus, as shown in Chemical Formula 3 or Chemical Formula 4, the second silane compound used in the cleaning solution according to the various embodiments of the present disclosure substitutes the hydroxy group bonded to the silicon particles present in the cleaning solution with a siloxane group in a form in which further polymerization is impossible at the time of cleaning the silicon substrate after the etching. Therefore, it is possible to prevent the silicon-based particles from growing and precipitating in micrometer sized silicon-based particles.

Here, the second silane compound preferably has a concentration of 100 to 5,000 ppm in the cleaning solution.

When the second silane compound in the cleaning solution is present at less than 100 ppm, an effect of suppressing the growth of nanometer-sized silicon-based particles into the micrometer-sized silicon-based particles during the cleaning process performed after etching the silicon substrate with the etching solution including the silicon additive may not be sufficient.

On the other hand, when the second silane compound in the cleaning solution is present at more than 5,000 ppm, there is a problem that it is difficult for the silane compound to be present in a sufficiently dissolved state in the cleaning solution.

As described above, the silane compound present in the cleaning solution may suppress a mechanism of the growth of the silicon-based particles at the time of cleaning performed after etching the silicon substrate with the etching solution including the silicon additive. Therefore, it is possible to prevent the growth and precipitation of silicon-based particles at the time of cleaning the silicon substrate after etching by using the cleaning solution according to the present disclosure.

As a result, defects in the silicon substrate and/or equipment caused by the silicon-based particles may be reduced.

Further, when the cleaning solution according to the present disclosure is used, the occurrence of the silicon-based particles at the time of cleaning may be reduced or suppressed even though the silicon substrate is etched with the etching solution including the silicon additive, and thus, the composition of the etching solution may be more easily designed. That is, there is no need to use other expensive additives as substitutes for the silicone additives.

According to another aspect of the present disclosure, there is provided a method of cleaning a substrate after etching capable of reducing or suppressing occurrence of silicon-based particles at the time of cleaning after a silicon substrate is etched with an etching solution including a silicon additive.

More specifically, the method of cleaning a substrate after etching according to an exemplary embodiment of the present disclosure includes a primary cleaning step of primarily cleaning the substrate etched with the etching solution including the silicon additive using a cleaning solution, and a secondary cleaning step of secondarily cleaning the primarily cleaned substrate using water.

The method of cleaning the substrate according to an exemplary embodiment of the present disclosure is based on a premise that the silicon substrate is etched with the etching solution including the silicon additive.

According to the present disclosure, the etched substrate is primarily cleaned with the acid aqueous solution including the second silane compound, and thus, the silicon-hydroxide group is substituted with the siloxane group in a form in which further polymerization is impossible, thereby preventing the growth and precipitation of the silicon-based particles into the micrometer-sized silicon-based particles.

Here, a temperature of the cleaning solution at the time of the primary cleaning of the etched substrate is preferably 70 to 160° C.

In general, the temperature of the etching solution used for etching is 150° C. or higher. Accordingly, when the temperature of the cleaning solution at the time of the primary cleaning is less than 70° C., the silicon substrate may be damaged due to rapid change in temperature of the silicon substrate. Further, when the temperature of the cleaning solution at the primary cleaning is more than 160° C., the silicon substrate may be damaged by excessive heat.

Subsequently, the primarily cleaned substrate is secondarily cleaned with water (for example, deionized water) to remove various contaminants from the silicon substrate.

Here, a temperature of the water at the time of the secondary cleaning of the primarily cleaned substrate is preferably 25 to 80° C.

Hereinafter, specific examples of the present disclosure will be provided. It is to be noted that Examples to be described below are provided merely for specifically exemplifying or explaining the present disclosure, and accordingly, the present disclosure is not limited to the following Examples.

Experimental Example 1. Data for Suppressing Silicon Oxide Particle Growth Example Compositions of the etching solutions for a silicon nitride layer according to Examples were shown in Table 1 below.

TABLE 1

| Classification | First silane compound (ppm) | Second silane compound (ppm) | Fluorine-containing compound (ppm) |
|---|---|---|---|
| Example 1 | 500 | 300 | 300 |
| Example 2 | 1,000 | 800 | 500 |
| Example 3 | 2,000 | 2,000 | 2,000 |
| Example 4 | 4,000 | 1,500 | 2,500 |
| Example 5 | 5,000 | 4,000 | 5,500 |
| Example 6 | 8,000 | 5,000 | 3,000 |
| Example 7 | 10,000 | 8,000 | 2,000 |
| Example 8 | 10,000 | 22,000 | 1,000 |

Each etching solution for a silicon nitride layer according to Examples 1 to 8 included 85% by weight of phosphoric acid 15% by weight of water, and included the first silane compound, the second silane compound, and the fluorine-containing compound in ppm units shown in Table 1 above.

Tetraethoxysilane as the first silane compound, trimethylhydroxylsilane as the second silane compound, and hydrogen fluoride as the fluorine-containing compound were used in Example 1.

Tetrahydroxysilane as the first silane compound, trimethylhydroxysilane as the second silane compound, and ammonium hydrogen fluoride as the fluorine-containing compound were used in Example 2.

Tetrahydroxysilane as the first silane compound, chlorotrimethylsilane as the second silane compound, and ammonium fluoride as the fluorine-containing compound were used in Example 3.

3-aminopropyltrihydroxysilane as the first silane compound, dichlorodimethylsilane as the second silane compound, and ammonium fluoride as the fluorine-containing compound were used in Example 4.

Hexahydroxydisiloxane as the first silane compound, 1,3-disiloxanediol as the second silane compound, and ammonium fluoride as the fluorine-containing compound were used in Example 5.

Trimethoxyhydroxysilane as the first silane compound, trimethylhydroxysilane as the second silane compound, and hydrogen fluoride as the fluorine-containing compound were used in Example 6.

Butyltrihydroxysilane as the first silane compound, trimethylhydroxysilane as the second silane compound, and hydrogen fluoride as the fluorine-containing compound were used in Example 7.

Tetrahydroxysilane as the first silane compound, chlorotrimethylsilane as the second silane compound, and hydrogen fluoride as the fluorine-containing compound were used in Example 8.

Comparative Example

Compositions of the etching solutions for a silicon nitride layer according to Comparative Examples were shown in Table 2 below.

TABLE 2

| Classification | First silane compound (ppm) | Fluorine-containing compound (ppm) |
|---|---|---|
| Comparative Example 1 | 500 | 400 |
| Comparative Example 2 | 500 | 500 |
| Comparative Example 3 | 500 | 700 |
| Comparative Example 4 | 500 | 500 |

Each etching solution for a silicon nitride layer according to Examples 1 to 4 included 85% by weight of phosphoric acid and a residual content of water, and included the first silane compound, and the fluorine-containing compound in ppm units shown in Table 1 above.

Terahydroxysilane as the first silane compound, and hydrogen fluoride as the fluorine-containing compound were used in Comparative Example 1.

Terahydroxysilane as the first silane compound, and ammonium hydrogen fluoride as the fluorine-containing compound were used in Comparative Example 2.

Tetrahydroxysilane as the first silane compound, and ammonium fluoride as the fluorine-containing compound were used in Example 3.

3-aminopropyltrihydroxysilane as the first silane compound, ammonium fluoride as the fluorine-containing compound were used in Comparative Example 4.

Experimental Results

Respective etching solutions for a silicon nitride layer having compositions of Examples and Comparative Examples were boiled at respective temperatures (145° C., 157° C., and 165° C.) for 0.5 h, 1 h, and 2 h, and the silicon nitride layers and the silicon oxide layers were etched for 1 minute. The silicon oxide layer, which is a thermally grown oxide layer, had an etching rate of 2 Å/min under a pure phosphoric acid solution at 165° C.

The silicon nitride layers and the silicon oxide layers were subjected to a planarization process before they were put into the etching solution, wherein the planarization process was performed by immersing the layers for 30 seconds in a hydrofluoric acid dilution prepared by diluting 50% by weight of hydrofluoric acid at a ratio of 200:1.

Each etching for etching temperature and etching time was completed, and then, each etching solution was analyzed by a particle size analyzer, and each average diameter of the silicon-based particles present in the etching solution was measured.

The etching rate was determined by calculating an average etching amount per minute by an ellipsometer after etching at 165° C. for 5 minutes.

The measurement results were shown in Tables 3 to 14 below.

TABLE 3

| Example 1 | 0.5 h | 1 h | 2 h |
|---|---|---|---|
| 165° C. | <0.01 μm | <0.01 μm | <0.01 μm |
| Etching amount (Å) at 165° C. per min | 1.4 | 1.3 | 1.4 |
| 157° C. | <0.01 μm | <0.01 μm | <0.01 μm |
| 145° C. | <0.01 μm | <0.01 μm | <0.01 μm |

TABLE 4

| Example 2 | 0.5 h | 1 h | 2 h |
|---|---|---|---|
| 165° C. | <0.01 μm | <0.01 μm | <0.01 μm |
| Etching amount (Å) at 165° C. per min | 1.7 | 1.7 | 1.8 |
| 157° C. | <0.01 μm | <0.01 μm | <0.01 μm |
| 145° C. | <0.01 μm | <0.01 μm | <0.01 μm |

TABLE 5

| Example 3 | 0.5 h | 1 h | 2 h |
|---|---|---|---|
| 165° C. | <0.01 μm | <0.01 μm | <0.01 μm |
| Etching amount (Å) at 165° C. per min | 2.0 | 2.1 | 1.9 |
| 157° C. | <0.01 μm | <0.01 μm | <0.01 μm |
| 145° C. | <0.01 μm | <0.01 μm | <0.01 μm |

TABLE 6

| Example 4 | 0.5 h | 1 h | 2 h |
|---|---|---|---|
| 165° C. | <0.01 μm | <0.01 μm | <0.01 μm |
| Etching amount (Å) at 165° C. per min | 1.8 | 1.8 | 1.7 |
| 157° C. | <0.01 μm | <0.01 μm | <0.01 μm |
| 145° C. | <0.01 μm | <0.01 μm | <0.01 μm |

TABLE 7

| Example 5 | 0.5 h | 1 h | 2 h |
|---|---|---|---|
| 165° C. | <0.01 μm | <0.01 μm | <0.01 μm |
| Etching amount (Å) at 165° C. per min | 1.9 | 1.8 | 1.8 |
| 157° C. | <0.01 μm | <0.01 μm | <0.01 μm |
| 145° C. | <0.01 μm | <0.01 μm | <0.01 μm |

TABLE 8

| Example 6 | 0.5 h | 1 h | 2 h |
|---|---|---|---|
| 165° C. | <0.01 μm | <0.01 μm | <0.01 μm |
| Etching amount (Å) at 165° C. per min | 1.7 | 1.7 | 1.8 |
| 157° C. | <0.01 μm | <0.01 μm | <0.01 μm |
| 145° C. | <0.01 μm | <0.01 μm | <0.01 μm |

TABLE 9

| Example 7 | 0.5 h | 1 h | 2 h |
|---|---|---|---|
| 165° C. | <0.01 μm | <0.01 μm | <0.01 μm |
| Etching amount (Å) at 165° C. per min | 1.9 | 2.0 | 2.0 |
| 157° C. | <0.01 μm | <0.01 μm | <0.01 μm |
| 145° C. | <0.01 μm | <0.01 μm | <0.01 μm |

TABLE 10

| Example 8 | 0.5 h | 1 h | 2 h |
|---|---|---|---|
| 165° C. | <0.01 μm | <0.01 μm | <0.01 μm |
| Etching amount (Å) at 165° C. per min | 1.8 | 1.8 | 1.8 |
| 157° C. | <0.01 μm | <0.01 μm | <0.01 μm |
| 145° C. | <0.01 μm | <0.01 μm | <0.01 μm |

Respective particle sizes of the etching solutions for a silicon nitride layer having compositions according to Examples 1 to 8 were analyzed, and as a result, it could be confirmed that silicon-based particles were not present in the etching solution or had an extremely small in diameter as 0.01 μm or less.

In particular, it could be confirmed that even when The etching solution capable of suppressing particle appearance was boiled at a high temperature for a long time, the silicon-based particles were hardly formed.

In addition, as a result of measuring an etching amount per minute at 165° C., it could be confirmed that the etching rate was similar to that of pure phosphoric acid even though the fluorine-containing compound was added in the etching solution.

On the other hand, particle sizes of the etching solutions for a silicon nitride layer having compositions according to Comparative Examples 1 to 4 were analyzed, and as a result, it was confirmed that silicon-based particles each having a diameter of 20 μm or more were present in the etching solution as shown in Tables 11 to 14 below.

Further, it could be confirmed that the etching amount per minute of the silicon oxide layer was increased by the fluorine-containing compound.

TABLE 11

| Comparative Example 1 | 0.5 h | 1 h | 2 h |
|---|---|---|---|
| 165° C. | 32.7 μm | 33.8 μm | 32.9 μm |
| Etching amount (Å) at 165° C. per min | 4.7 | 4.5 | 4.2 |
| 157° C. | 26.8 μm | 29.4 μm | 29.7 μm |
| 145° C. | 23.5 μm | 24.3 μm | 24.5 μm |

TABLE 12

| Comparative Example 2 | 0.5 h | 1 h | 2 h |
|---|---|---|---|
| 165° C. | 53.7 μm | 55.4 μm | 54.8 μm |
| Etching amount (Å) at 165° C. per min | 5.2 | 5.1 | 4.8 |
| 157° C. | 48.3 μm | 47.7 μm | 49.3 μm |
| 145° C. | 41.3 μm | 42.2 μm | 44.4 μm |

TABLE 13

| Comparative Example 3 | 0.5 h | 1 h | 2 h |
|---|---|---|---|
| 165° C. | 44.8 μm | 45.7 μm | 48.1 μm |
| Etching amount (Å) at 165° C. per min | 7.8 | 7.4 | 7.3 |
| 157° C. | 39.8 μm | 41.1 μm | 41.5 μm |
| 145° C. | 38.1 μm | 38.8 μm | 40.6 μm |

TABLE 14

| Comparative Example 4 | 0.5 h | 1 h | 2 h |
|---|---|---|---|
| 165° C. | 35.3 μm | 36.6 μm | 37.0 μm |
| Etching amount (Å) at 165° C. per min | 6.3 | 6.2 | 6.1 |
| 157° C. | 33.1 μm | 32.8 μm | 34.3 μm |
| 145° C. | 29.1 μm | 30.7 μm | 31.5 μm |

Experimental Example 2. Post-Etching Cleaning Solution

Experimental Results 1

Before a silicon substrate including the silicon nitride layer was put into the etching solution, the silicon substrate was immersed for 30 seconds in a solution prepared by diluting 50% by weight of hydrofluoric acid at a ratio of 200:1 to perform planarization.

Next, the planarized silicon substrate was etched for 5 minutes with an 85% aqueous phosphoric acid solution including 500 ppm of tetrahydroxysilane and 500 ppm of ammonium fluoride ($NH_4F$), and then, primarily cleaned for 10 seconds with cleaning solutions at 80° C. each having a composition according to each of Examples and Comparative Examples, followed by secondary cleaning for 30 seconds with deionized water at 80° C.

The cleaning solution after the primary cleaning was completed, and the deionized water after the secondary cleaning was completed were extracted, respectively, and average diameters of the silicon-based particles present in the cleaning solution and the deionized water were measured by a particle size analyzer.

Table 15 below shows the compositions of the cleaning solutions of Examples 9 and 10 and Comparative Examples 5 to 7, and the measurement results of the average diameters of the silicon-based particles present in the cleaning solution and the deionized water after cleaning.

TABLE 15

| Classification | Composition of cleaning solution | Average diameter of silicon-based particles in cleaning solution | Average diameter of silicon-based particles in deionized water |
|---|---|---|---|
| Example 9 | 85 wt % Phosphoric acid/ Trimethylsilanol 500 ppm/ Residual water | <0.1 μm | <0.1 μm |
| Example 10 | 85 wt % Phosphoric acid/ Dimethyldisilanol 500 ppm/ Residual water | <0.1 μm | <0.1 μm |
| Comparative Example 5 | Deionized water | 138 μm | 153 μm |
| Comparative Example 6 | 85 wt % Phosphoric acid/ Residual water | 7.3 μm | 4.8 μm |
| Comparative Example 7 | 85 wt % Phosphoric acid/ Polyoxyethylene alkylether phosphate 500 ppm/ Residual water | 5.8 μm | 6.5 μm |

Experimental Results 2

Before a silicon substrate including the silicon nitride layer was put into the etching solution, the silicon substrate was immersed for 30 seconds in a solution prepared by diluting 50% by weight of hydrofluoric acid at a ratio of 200:1 to perform planarization.

Next, the planarized silicon substrate was etched for 5 minutes with an 85% aqueous phosphoric acid solution including 500 ppm of 3-aminopropylsilanetriol and 500 ppm of ammonium fluoride ($NH_4F$), and then, primarily cleaned for 10 seconds with cleaning solutions at 80° C. each having a composition according to each of Examples and Comparative Examples, followed by secondary cleaning for 30 seconds with deionized water at 80° C.

The cleaning solution after the primary cleaning was completed, and the deionized water after the secondary cleaning was completed were extracted, respectively, and average diameters of the silicon-based particles present in the cleaning solution and the deionized water were measured by a particle size analyzer.

Table 16 below shows the compositions of the cleaning solutions of Examples 11 and 13 and Comparative Examples 8 to 10, and the measurement results of the average diameters of the silicon-based particles present in the cleaning solution and the deionized water after cleaning.

TABLE 16

| Classification | Composition of cleaning solution | Average diameter of silicon-based particles in cleaning solution | Average diameter of silicon-based particles in deionized water |
|---|---|---|---|
| Example 11 | 85 wt % Phosphoric acid/ Trimethylsilanol 500 ppm/ Residual water | <0.1 μm | <0.1 μm |
| Example 12 | 90 wt % Sulfuric acid/ Dimethylsilanediol 500 ppm/ Residual water | <0.1 μm | <0.1 μm |
| Example 13 | 90 wt % acetic acid/1-chlorotrimethylsilane 500 ppm/Residual water | <0.1 μm | <0.1 μm |
| Comparative Example 8 | Deionized water | 118 μm | 174 μm |
| Comparative Example 9 | 85 wt % Phosphoric acid/ Residual water | 5.3 μm | 6.2 μm |
| Comparative Example 10 | 85 wt % Phosphoric acid/ Polyoxyethylene alkylether phosphate 500 ppm/ Residual water | 4.4 μm | 7.35 μm |

Experimental Results 3

Before a silicon substrate including the silicon nitride layer was put into the etching solution, the silicon substrate was immersed for 30 seconds in a solution prepared by diluting 50% by weight of hydrofluoric acid at a ratio of 200:1 to perform planarization.

Next, the planarized silicon substrate was etched for 5 minutes with an 80% aqueous phosphoric acid solution including 500 ppm of 3-aminopropylsilanetriol and 500 ppm of ammonium fluoride ($NH_4F$), and then, primarily cleaned for 10 seconds with cleaning solutions at 80° C. each having a composition according to each of Examples and Comparative Examples, followed by secondary cleaning for 30 seconds with deionized water at 80° C.

The cleaning solution after the primary cleaning was completed, and the deionized water after the secondary cleaning was completed were extracted, respectively, and average diameters of the silicon-based particles present in the cleaning solution and the deionized water were measured by a particle size analyzer.

Table 17 below shows the compositions of the cleaning solutions of Example 14 and Comparative Example 11, and the measurement results of the average diameters of the silicon-based particles present in the cleaning solution and the deionized water after cleaning.

TABLE 17

| Classification | Composition of cleaning solution | Average diameter of silicon-based particles in cleaning solution | Average diameter of silicon-based particles in deionized water |
|---|---|---|---|
| Example 14 | 80 wt % Phosphoric acid/ Trimethylsilanol 500 ppm/ Residual water | <0.1 μm | <0.1 μm |

TABLE 17-continued

| Classification | Composition of cleaning solution | Average diameter of silicon-based particles in cleaning solution | Average diameter of silicon-based particles in deionized water |
|---|---|---|---|
| Comparative Example 11 | 60 wt % Phosphoric acid/ Trimethylsilanol 500 ppm/ Residual water | 34.4 μm | 31.3 μm |

Experimental Results 4

Before a silicon substrate including the silicon nitride layer was put into the etching solution, the silicon substrate was immersed for 30 seconds in a solution prepared by diluting 50% by weight of hydrofluoric acid at a ratio of 200:1 to perform planarization.

Next, the planarized silicon substrate was etched for 5 minutes with an 80% aqueous phosphoric acid solution including 500 ppm of tetrahydroxysilane and 500 ppm of ammonium fluoride ($NH_4F$), and then, primarily cleaned for 10 seconds with cleaning solutions at 80° C. each having a composition according to each of Examples and Comparative Examples, followed by secondary cleaning for 30 seconds with deionized water at 80° C.

The cleaning solution after the primary cleaning was completed, and the deionized water after the secondary cleaning was completed were extracted, respectively, and average diameters of the silicon-based particles present in the cleaning solution and the deionized water were measured by a particle size analyzer.

Table 18 below shows the compositions of the cleaning solutions of Examples 15 and 16 and Comparative Example 12, and the measurement results of the average diameters of the silicon-based particles present in the cleaning solution and the deionized water after cleaning.

TABLE 18

| Classification | Composition of cleaning solution | Average diameter of silicon-based particles in cleaning solution | Average diameter of silicon-based particles in deionized water |
|---|---|---|---|
| Example 15 | 90 wt % Sulfuric acid/ Dimethylsilanediol 1500 ppm/ Residual water | <0.1 μm | <0.1 μm |
| Example 16 | 90 wt % Sulfuric acid/ Dimethylsilanediol 3000 ppm/ Residual water | <0.1 μm | <0.1 μm |
| Comparative Example 12 | 90 wt % Sulfuric acid/ Dimethylsilanediol 50 ppm/ Residual water | 1.3 μm | 0.8 μm |

Experimental Results 5

Before a silicon substrate including the silicon nitride layer was put into the etching solution, the silicon substrate was immersed for 30 seconds in a solution prepared by diluting 50% by weight of hydrofluoric acid at a ratio of 200:1 to perform planarization.

Next, the planarized silicon substrate was etched for 5 minutes with an 80% aqueous phosphoric acid solution including 500 ppm of tetrahydroxysilane and 500 ppm of ammonium fluoride ($NH_4F$), and then, primarily cleaned for 10 seconds with cleaning solutions at various temperatures each having a composition according to each of Examples and Comparative Examples, followed by secondary cleaning for 30 seconds with deionized water at various temperatures.

The cleaning solution after the primary cleaning was completed, and the deionized water after the secondary cleaning was completed were extracted, respectively, and average diameters of the silicon-based particles present in the cleaning solution and the deionized water were measured by a particle size analyzer.

Table 19 below shows the compositions of the cleaning solutions of Examples 17 and 18 and Comparative Examples 13 to 14, and the measurement results of the average diameters of the silicon-based particles present in the cleaning solution and the deionized water after cleaning.

TABLE 19

| Classification | Composition and temperature of cleaning solution | Temperature of deionized water | Average diameter of silicon-based particles in cleaning solution | Average diameter of silicon-based particles in deionized water |
|---|---|---|---|---|
| Example 17 | 85 wt % Phosphoric acid/ Trimethylsilanol 500 ppm/Residual water 100° C. | 80° C. | <0.1 μm | <0.1 μm |

TABLE 19-continued

| Classification | Composition and temperature of cleaning solution | Temperature of deionized water | Average diameter of silicon-based particles in cleaning solution | Average diameter of silicon-based particles in deionized water |
|---|---|---|---|---|
| Example 18 | 85 wt % Phosphoric acid/ Trimethylsilanol 500 ppm/Residual water 140° C. | 80° C. | <0.1 µm | <0.1 µm |
| Comparative Example 13 | 85 wt % Phosphoric acid/ Trimethylsilanol 500 ppm/Residual water 140° C. | 80° C. | <0.1 µm | Silicon substrate damaged |
| Comparative Example 14 | 85 wt % Phosphoric acid/ Trimethylsilanol 500 ppm/Residual water 25° C. | — | Silicon substrate damaged | — |

The etching solution capable of suppressing particle appearance according to the present disclosure may include the silane compound-based silicon additive to be able to increase the selectivity of the silicon nitride layer to the silicon oxide layer, and may further include the fluorine-containing compound to be able to compensate for the etching rate reduced due to the use of the silicon additive.

In addition, The etching solution capable of suppressing particle appearance according to the present disclosure uses different kinds of silane compounds having different numbers of hydrophilic functional groups bonded to silicon atoms, and thus, it is possible to prevent the etching rate of the silicon oxide layer from increasing due to the excess fluorine present in the etching solution.

Further, since The etching solution capable of suppressing particle appearance according to the present disclosure is able to effectively suppress the occurrence of silicon-based particles, defects of the silicon substrate or failure of the etching device and the cleaning device caused by the occurrence of the silicon-based particles during etching or during cleaning after etching may be prevented.

In particular, according to the present disclosure, the silane compound represented by Chemical Formula 3 may substitute the hydroxy group of the silicon particle including the hydroxy group present in the cleaning solution with a siloxane group in a form in which further polymerization is impossible at the time of cleaning the silicon substrate after the etching, and thus, it is possible to prevent growth and precipitation of the silicon-based particles.

The present disclosure described above may be variously substituted, altered, and modified by those skilled in the art to which the present invention pertains without departing from the scope and sprit of the present disclosure. Therefore, the present disclosure is not limited to the above-mentioned exemplary embodiments and the accompanying drawings.

What is claimed is:

1. An etching solution for suppressing particle appearance comprising:
   an aqueous solution including phosphoric acid;
   a first silane compound including 1 to 6 silicon atoms where at least one silicon atom is bonded to three or more hydrophilic functional groups, wherein a concentration of the first silane compound in the etching solution ranges from 100 ppm to 10,000 ppm;
   a second silane compound including 1 to 6 silicon atoms where the number of hydrophilic functional groups bonded to one silicon atom is a maximum of 2, wherein a concentration of the second silane compound in the etching solution ranges from 100 ppm to 30,000 ppm; and
   a fluorine-containing compound.

2. The etching solution capable of suppressing particle appearance of claim 1, wherein the hydrophilic functional group is a hydroxyl or a functional group substitutable with a hydroxyl group under a pH condition of the etching solution,
   wherein the functional group substitutable with a hydroxy group under a pH condition of the etching solution is selected from the group consisting of an amino group, a halogen group, a sulfonic group, a phosphonic group, a phosphoric group, a thiol group, an alkoxy group, an amide group, an ester group, an acid anhydride group, an acyl halide group, a cyano group, a carboxyl group, and an azole group.

3. The etching solution capable of suppressing particle appearance of claim 1, wherein the first silane compound is represented by Chemical Formula 1 below or Chemical Formula 2 below:

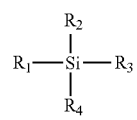

[Chemical Formula 1]

in Chemical Formula 1, $R_1$ to $R_4$ are each independently a hydrophilic functional group or a functional group selected from the group consisting of hydrogen, $C_1$-$C_{10}$ alkyl, $C_6$-$C_{12}$ cycloalkyl, $C_2$-$C_{10}$ heteroalkyl including at least one heteroatom, $C_2$-$C_{10}$ alkenyl, $C_2$-$C_{10}$ alkynyl, $C_1$-$C_{10}$ haloalkyl, $C_1$-$C_{10}$ aminoalkyl, aryl, heteroaryl, aralkyl, silyloxy, and siloxane, and

[Chemical Formula 2]

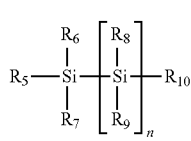

in Chemical Formula 2, $R_5$ to $R_{20}$ are each independently a hydrophilic functional group or a functional group selected from the group consisting of hydrogen, $C_1$-$C_{10}$ alkyl, $C_6$-$C_{12}$ cycloalkyl, $C_2$-$C_{10}$ heteroalkyl including at least one heteroatom, $C_2$-$C_{10}$ alkenyl, $C_2$-$C_{10}$ alkynyl, $C_1$-$C_{10}$ haloalkyl, $C_1$-$C_{10}$ aminoalkyl, aryl, heteroaryl, aralkyl, silyloxy, and siloxane, and n is an integer of 1 to 5.

4. The etching solution capable of suppressing particle appearance of claim 3, wherein the hydrophilic functional group is selected from the group consisting of a hydroxyl group, an amino group, a halogen group, a sulfonic group, a phosphonic group, a phosphoric group, a thiol group, an alkoxy group, an amide group, an ester group, an acid anhydride group, an acyl halide group, a cyano group, a carboxyl group, and an azole group.

5. The etching solution capable of suppressing particle appearance of claim 1, wherein the second silane compound is represented by Chemical Formula 3 below or Chemical Formula 4 below:

[Chemical Formula 3]

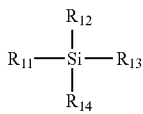

in Chemical Formula 3, $R_{11}$ to $R_{14}$ are each independently a hydrophilic functional group or a functional group selected from the group consisting of hydrogen, $C_1$-$C_{10}$ alkyl, $C_6$-$C_{12}$ cycloalkyl, $C_2$-$C_{10}$ heteroalkyl including at least one heteroatom, $C_2$-$C_{10}$ alkenyl, $C_2$-$C_{10}$ alkynyl, $C_1$-$C_{10}$ haloalkyl, $C_1$-$C_{10}$ aminoalkyl, aryl, heteroaryl, aralkyl, silyloxy, and siloxane, and

[Chemical Formula 4]

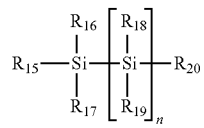

in Chemical Formula 4, $R_{15}$ to $R_{20}$ are each independently a hydrophilic functional group or a functional group selected from the group consisting of hydrogen, $C_1$-$C_{10}$ alkyl, $C_6$-$C_{12}$ cycloalkyl, $C_2$-$C_{10}$ heteroalkyl including at least one heteroatom, $C_2$-$C_{10}$ alkenyl, $C_2$-$C_{10}$ alkynyl, $C_1$-$C_{10}$ haloalkyl, $C_1$-$C_{10}$ aminoalkyl, aryl, heteroaryl, aralkyl, silyloxy, and siloxane, and n is an integer of 1 to 5.

6. The etching solution capable of suppressing particle appearance of claim 5, wherein the hydrophilic functional group is selected from the group consisting of a hydroxyl group, an amino group, a halogen group, a sulfonic group, a phosphonic group, a phosphoric group, a thiol group, an alkoxy group, an amide group, an ester group, an acid anhydride group, an acyl halide group, a cyano group, a carboxyl group, and an azole group.

7. The etching solution capable of suppressing particle appearance of claim 1, wherein the fluorine-containing compound is at least one selected from the group consisting of hydrogen fluoride, ammonium fluoride, ammonium bifluoride, and ammonium hydrogen fluoride.

8. The etching solution capable of suppressing particle appearance of claim 1, wherein the fluorine-containing compound is a compound in which an organic cation and a fluorine-based anion are ionically bonded.

9. The etching solution capable of suppressing particle appearance of claim 8, wherein the organic cation is selected from the group consisting of alkylammonium, alkylpyrrolium, alkylimidazolium, alkylpyrazolium, alkyloxazolium, alkylthiazolium, alkylpyridinium, alkylpyrimidinium, alkylpyridazinium, alkylpyrazinium, alkylpyrrolidinium, alkylphosphonium, alkylmorpholinium, and alkylpiperidinium.

10. The etching solution capable of suppressing particle appearance of claim 8, wherein the fluorine-based anion is selected from the group consisting of fluoride, fluorophosphate, fluoroalkyl-fluorophosphate, fluoroborate, and fluoroalkyl-fluoroborate.

* * * * *